United States Patent
Kupferschmid et al.

(10) Patent No.: US 6,702,818 B2
(45) Date of Patent: Mar. 9, 2004

(54) SURGICAL DRILLING DEVICE FOR PERFORATING THE CRANIUM

(75) Inventors: Bernhard Kupferschmid, Emmingen-Liptingen (DE); Dieter Weisshaupt, Immendingen (DE); Karl-Dieter Lerch, Witten (DE)

(73) Assignee: Aesculap AG & Co. KG, Tuttlingen (DE)

( * ) Notice: Subject to any disclaimer, the term of this patent is extended or adjusted under 35 U.S.C. 154(b) by 401 days.

(21) Appl. No.: 09/751,340

(22) Filed: Dec. 28, 2000

(65) Prior Publication Data

US 2001/0016744 A1 Aug. 23, 2001

Related U.S. Application Data

(63) Continuation of application No. PCT/EP99/03496, filed on May 21, 1999.

(30) Foreign Application Priority Data

Jul. 1, 1998 (DE) ......................... 198 29 406

(51) Int. Cl.⁷ .............................................. A61B 17/16
(52) U.S. Cl. ........................................ 606/80; 606/96
(58) Field of Search .................. 606/79–81, 96–98; 408/241 G, 241 S

(56) References Cited

U.S. PATENT DOCUMENTS

| | | | |
|---|---|---|---|
| 2,525,669 A | * 10/1950 | Hainault | 606/96 |
| 4,319,577 A | 3/1982 | Bofinger et al. | |
| 4,821,716 A | 4/1989 | Ghajar et al. | |
| 5,207,681 A | * 5/1993 | Ghadjar et al. | 606/96 |

FOREIGN PATENT DOCUMENTS

| | | |
|---|---|---|
| DE | 29 16 221 | 3/1980 |
| DE | 298 11 640 | 9/1998 |

* cited by examiner

Primary Examiner—Julian W. Woo
(74) Attorney, Agent, or Firm—Barry L. Lipsitz; Douglas M. McAllister

(57) ABSTRACT

In order to improve the quality of the drilling process in a surgical drilling apparatus for perforating the cranium including a drill plate which can be placed upon the cranium and a drill which is guided in the drill plate, it is proposed that the drill be accommodated in a mounting which is rotatably mounted on the drill plate, said drill being displaceable along the rotational axis and being accommodated so as to be non-rotatable relative to said mounting, and in that the drill be displaceable towards the mounting against the effect of a spring.

14 Claims, 1 Drawing Sheet

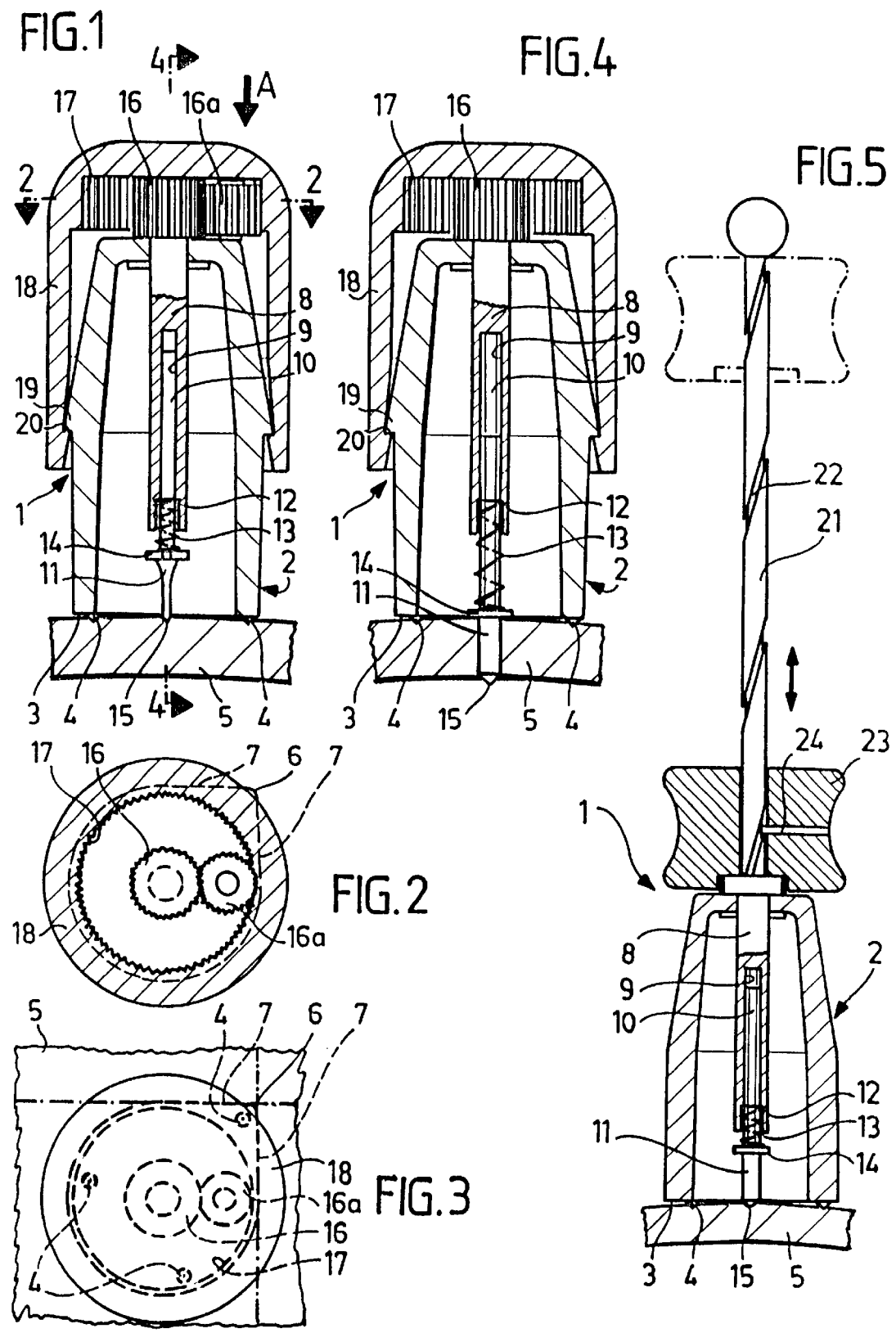

SURGICAL DRILLING DEVICE FOR PERFORATING THE CRANIUM

This application is a continuation of international application No. PCT/EP99/03496 filed on May 21, 1999.

The invention relates to a surgical drilling apparatus for perforating the cranium including a drill plate which can be placed upon the cranium and a drill which is guided in the drill plate.

Drilling apparatus of this type are needed when it is necessary to install a ventricle drainage system so as to relieve the pressure in the interior of the skull for example. Hereby, it is known to use drill plates through which a drill provided with a handpiece is inserted (U.S. Pat. No. 4,821,716). With these, the operator presses the drill against the cranium and the drill is rotated until the skull has been penetrated. However, there is a danger here that avoidable injuries may be produced by maladroit application of pressure to the hand drill.

The object of the invention is to design a surgical drilling apparatus of the above type such that, when using it during the drilling process, injuries will be avoided in so far as possible.

In accordance with the invention, this object is achieved in the case of a surgical drilling apparatus of the type mentioned hereinabove, in that the drill is accommodated in a mounting which is rotatably mounted on the drill plate, said drill being displaceable along the rotational axis and being accommodated so as to be non-rotatable relative to said mounting, and in that the drill is displaceable towards the mounting against the effect of a spring.

Consequently, by virtue of such a design, the drill is pressed against the cranium with a defined spring force so that the axial force effective on the drill is independent of how strongly the user presses the drill plate and a drive means for the drill against the cranium. The pressure applied by the drill is determined by the spring alone, and consequently is selectable such as to ensure that cerebral tissue located below the cranium will be subjected to as little injury as possible.

It is expedient if a stop is provided for limiting the displacement of the drill relative to the mounting produced by the effect of the spring. It is thereby ensured that the drill is held captive in the mounting in an axial direction prior to the drill being placed on the cranium.

Furthermore, it is advantageous if the drill carries a stop for limiting the drilling depth, for example, in the form of a flange which can be placed on the upper surface of the cranium. This stop limits the depth to which the drill can penetrate into the cranium and can be selected such that the cranium will just be penetrated without the drill thereby entering substantially into the underlying cranial tissue and thus causing injuries thereto.

In a preferred embodiment, the mounting comprises a blind bore for accommodating the drill. The resultant construction is thereby very compact. It is expedient hereby if a spring, which pushes the drill out therefrom, is disposed in the blind bore i.e. the spring which presses the drill against the cranium with the desired spring force.

The drill may be driven in various manners, possibly by means of a motor, but in most cases the drive will be effected manually.

Thus, provision may be made for the mounting to be provided with a threaded guide means for a handpiece which engages the threaded guide means and is mounted thereon such as to be longitudinally displaceable therealong. Such a handpiece can be moved backwards and forwards along the threaded guide means thereby rotating the mounting and hence the drill.

In another embodiment, provision is made for the mounting to carry a gear wheel that engages directly or indirectly with a crown wheel which is rotatably mounted on the drill plate and is rotatable by means of a handle element.

It is expedient hereby if the crown wheel is disposed on the inner wall of a cap shaped handle element which surrounds the drill plate. Such a drill plate is thus of very compact construction and, moreover, it is also provided with an integral drive means for the drill.

The drill plate may, for example, be in the form of a cylinder and may comprise a plurality of support feet for resting it on the cranium whereby, in particular, three support feet may be provided.

In accordance with a preferred embodiment, provision is made for the drill plate to carry a marking element around its periphery for the purposes of positioning it on the cranium. This marking element enables the surgeon to place the drill plate on the cranium at a very specific position thereby ensuring that the drilling process will take place at the desired spot.

In particular, the marking element may comprise two right-angled delimiting lines. These delimiting lines can be aligned with corresponding marking lines which the surgeon has drawn on the cranium, for example, these marking lines could be connecting lines extending from ear to ear on the one hand and connecting lines extending at right angles thereto from the root of the nose to the centre of the back of the head. If the corner of the right-angled marking element is placed exactly at the crossing point of the two lines, and if the delimiting lines extend exactly in parallel with the connecting lines, then the precise position for the drill plate on the cranium is defined.

It would also be possible for the drill plate to comprise a lateral projection having side faces extending at right angles to one another, and for the side faces to flow tangentially into the outer contour of the drill plate. This could be effected over the whole height of the housing for the drill plate, but provision could be made for the projection to be provided only in the region of a flange on the drill plate on the side thereof facing the skull.

The following description of preferred embodiments of the invention in conjunction with the drawing will serve to provide a more detailed explanation. Therein FIG. 1 shows a longitudinal sectional view of a drill placed on the cranium incorporating a resiliently insertable drill at the beginning of the drilling process;

FIG. 2 shows a sectional view along the line 2—2 in FIG. 1;

FIG. 3 shows a top view of the drill in FIG. 1 in the direction of the arrow A;

FIG. 4 shows a sectional view along the line 4—4 in FIG. 1 with the drill in the position it occupies following the ending of the drilling process and FIG. 5 shows a view similar to FIG. 1 of another preferred embodiment of a surgical drill.

The drilling apparatus 1 illustrated in FIGS. 1 to 4 of the drawing comprises a pot shaped housing 2 which comprises three pointed projections 4 distributed over the periphery of its lower rim 3, said projections 4 being used for placing the housing 2 on a cranium 5. The housing 2 has a circular cross-section, although a portion thereof sticks out at one side in the form of a projection 6 that is bounded by side faces 7 which extend at right angles to one another and which flow tangentially into the periphery of the cylindrical part of the housing 2. Thus, in the region of the rim 3, this results in a cross-section which is circular over 270°, whereas the remaining peripheral region projects out at right angles. This projection 6 serves as a marking element so that, for example, the housing can be exactly positioned on the cranium by placing the side faces 7 on some right-angled marking lines drawn thereon (FIG. 3).

A rod shaped mounting 8 is mounted in the upper part of the closed housing 2 so as to be axially non-displaceable although rotatable about the longitudinal axis of the housing 2, said mounting 8 comprising a central blind hole 9 which is open at its lower end and into which the shaft 10 of a drill 11 projects. The shaft 10 is accommodated in the blind hole 9 so as to be freely displaceable in the axial direction, but the shaft 10 is not rotatable relative to the mounting 8. This can be achieved by appropriate shaping of the cross-section of the shaft 10 and of the blind hole 9, or, by means of a suitable chuck device.

A helical spring 13 surrounding the shaft 10 is supported on a step 12 in the blind hole 9 whilst the other end of the spring rests on an annular flange 14 on the drill 11. This annular flange 14 simultaneously forms a bottom stop for the drill 11, whereby the length of the drill 11 from its tip 15 to the annular flange 14 substantially corresponds to the thickness of the cranium 5 through which a hole is to be bored.

A corresponding stop is provided for preventing the shaft 10 from falling out of the blind hole 9, although this is not illustrated in the drawing.

The mounting 8 projects upwardly out of the housing 2 and there, it carries a pinion 16 that meshes with another pinion 16a which is rotatable on the housing 2 about a parallel rotational axis.

In turn, the pinion 16a engages in an inner crown wheel 17 of a cap 18 which surrounds the upper end of the housing 2 and is rotatable about the central axis of the housing 2, said cap being attached to the housing 2 in the axial direction, for example, by means of a latching connection 19, 20.

If one rotates the cap 18 relative to the housing 2 then this rotational connection is conveyed via the two pinions 16a and 16 and thus to the mounting 8 and thus to the drill 11.

In order to produce a drilling, the right-angled projection 6 of the drill 11 is placed on the marking lines on the upper surface of the cranium in the desired manner, whereby the drill will then be exactly positioned. By virtue of axial pressure on the housing 2, the pointed projections 6 dig slightly into the cranium 5 and thus fix the position of the housing 2. The tip 15 of the drill 11 thereby rests on the outer surface of the cranium 5 under the effect of the helical spring 13 and it will dig in when the drill is rotated so as to form a bore in the cranium 5. The forward movement is thereby determined exclusively by the helical spring 13 until such time as the annular flange 14 comes to rest on the outer surface of the cranium 5 and thus limits the depth of penetration of the drill 11. The cranium 5 is penetrated by a precise amount in this manner without damaging the underlying cranial tissue.

The embodiment of FIG. 5 is generally similar to that of FIGS. 1 to 4, so that similar parts bear the same reference symbols.

Here, in contrast to the embodiment of FIGS. 1 to 4, another drive system is provided for the mounting 8, whereby the cap 18 and its inner crown wheel 17 as well as the two pinions 16 and 16a are dispensed with. In this embodiment, the mounting 8 is more in the form of a long shaft 21 which extends upwardly and it comprises a steep thread-groove 22 upon which there is mounted an annular handle element 23 whose height can be varied. A projection 24 on the handle element engages in the thread-groove 22 so that the shaft 21 will rotate when the handle element is displaced vertically therealong. Due to the vertical displacement of the handle element 23, the drill 11 can thus be rotated in the desired manner.

What is claimed is:

1. A surgical drilling apparatus for perforating the cranium, comprising:
   a drill plate which can be placed upon the cranium, and
   a drill which is guided in the drill plate, wherein:
      the drill is accommodated in a mounting which is rotatably mounted on the drill plate, said drill being displaceable along a rotational axis and being accommodated so as to be non-rotatable relative to said mounting,
      the drill is displaceable towards the mounting against the effect of a spring, and
      the mounting comprises a blind bore for accommodating the drill.

2. A surgical drilling apparatus in accordance with claim 1, wherein there is provided a stop for limiting the displacement of the drill relative to the mounting produced by the effect of the spring.

3. A surgical drilling apparatus in accordance with claim 2, wherein the drill carries a stop for limiting the drilling depth.

4. A surgical drilling apparatus in accordance with claim 1, wherein said spring, which pushes the drill out therefrom, is disposed in the blind bore.

5. A surgical drilling apparatus in accordance with claim 1, wherein the drill plate is in the form of a cylinder and comprises a plurality of support feet for resting it on the cranium.

6. A surgical drilling apparatus in accordance with claim 5, wherein three support feet are provided.

7. A surgical drilling apparatus in accordance with claim 1, wherein the drill plate carries a marking element around its periphery for the purposes of positioning it on the cranium.

8. A surgical drilling apparatus in accordance with claim 7, wherein the marking element comprises two right-angled delimiting lines.

9. A surgical drilling apparatus for perforating the cranium, comprising:
   a drill plate which can be placed upon the cranium, and
   a drill which is guided in the drill plate, wherein:
      the drill is accommodated in a mounting which is rotatably mounted on the drill plate, said drill being displaceable along a rotational axis and being accommodated so as to be non-rotatable relative to said mounting,
      the drill is displaceable towards the mounting against the effect of a spring, and
      the mounting is provided with a threaded guide means for a handpiece which engages the threaded guide means and is mounted thereon such as to be longitudinally displaceable therealong.

10. A surgical drilling apparatus in accordance with claim 9, wherein the mounting comprises a blind bore for accommodating the drill.

11. A surgical drilling apparatus for perforating the cranium, comprising:
    a drill plate which can be placed upon the cranium, and
    a drill which is guided in the drill plate, wherein:
       the drill is accommodated in a mounting which is rotatably mounted on the drill plate, said drill being displaceable along a rotational axis and being accommodated so as to be non-rotatable relative to said mounting, the drill is displaceable towards the mounting against the effect of a spring, and the mounting carries a gear wheel that meshes with a crown wheel which is rotatably mounted on the drill plate and is rotatable by means of a handle element.

12. A surgical drilling apparatus in accordance with claim 11, wherein the crown wheel is disposed on the inner side of a cap-like handle element which surrounds the drill plate.

13. A surgical drilling apparatus for perforating the cranium, comprising:

a drill plate which can be placed upon the cranium, and a drill which is guided in the drill plate, wherein:

the drill is accommodated in a mounting which is rotatably mounted on the drill plate, said drill being displaceable along a rotational axis and being accommodated so as to be non-rotatable relative to said mounting, the drill is displaceable towards the mounting against the effect of a spring, and the drill plate comprises a lateral projection having side faces extending at right angles to one another, and in that the side faces flow tangentially into the outer contour of the drill plate.

14. A surgical drilling apparatus in accordance with claim 13, wherein the projection is only provided in a region of a flange on the drill plate on a side thereof configured to face a surface to be drilled.

* * * * *